United States Patent [19]
Bjorkholm

[11] Patent Number: 4,807,637
[45] Date of Patent: Feb. 28, 1989

[54] DIAPHANOGRAPHY METHOD AND APPARATUS

[75] Inventor: Paul J. Bjorkholm, Sharon, Mass.

[73] Assignee: American Science and Engineering, Inc., Cambridge, Mass.

[21] Appl. No.: 861,200

[22] Filed: May 8, 1986

Related U.S. Application Data

[63] Continuation of Ser. No. 642,228, Aug. 20, 1984, abandoned.

[51] Int. Cl.4 .................... A61B 6/08; A61B 6/12
[52] U.S. Cl. ............................. 128/664; 128/665; 250/358.1; 250/341; 250/360.1; 378/37
[58] Field of Search ............... 128/633, 664, 665, 653, 128/23; 378/37; 250/341, 358.1, 360.1

[56] References Cited

U.S. PATENT DOCUMENTS 4,203,037 5/1980 Gur et al. .................... 378/37
4,212,306 7/1980 Mahmud ..................... 128/665
4,515,165 5/1985 Carroll ..................... 128/665 X Primary Examiner—Kyle L. Howell
Assistant Examiner—John C. Hanley
Attorney, Agent, or Firm—Pollock, Vande Sande & Priddy

[57] ABSTRACT

A method and apparatus for practicing diaphanography by directing a beam of collimated light along a linear input path into incidence with a flat side of a compressed human breast, and collecting light which emerges from an opposing flat side of the compressed breast along an output path that is colinear with the light input path and with an angular divergence no greater than the angular divergence of the collimated input beam of light. Application of a good scatter rejecting geometry assures that the useful information in that portion of the beam of light which passes directly through the compressed breast can be utilized even though the emergent light is only a small fraction of the incident light.

31 Claims, 1 Drawing Sheet

DIAPHANOGRAPHY METHOD AND APPARATUS

This is a continuation of co-pending application Ser. No. 642,228, filed on Aug. 20, 1984, now abandoned.

BACKGROUND OF THE INVENTION

Diaphanography is a technique which has been suggested heretofore wherein a human breast is transilluminated with optical or near optical wavelength radiation to produce an image on photographic film for the purpose of detecting lesions. Various approaches to this technique have been proposed, including real time optical viewing, image intensification, video viewing, etc. All of these techniques have the common problem of light scatter, i.e., a very large fraction of the light entering the breast is scattered one or more times prior to exiting the breast. The number of scatters per photon can be quite high and, as a result, the light exiting the breast carriers little or no information about the entrance side of the breast tissue because of the number of scatterings. This has limited diaphanography to imaging the region near the exit plane, and good results have been obtained only by manipulation of the tissue to bring the region of interest as close to the surface as possible.

It has been shown that about $10^{-4}$ of the light incident on a 6 cm. compressed breast will be transmitted without scatter. This means that the mean free path length in a breast is about 0.65 cm., and any object more than 1 cm. below the skin line will be very difficult to detect. Its shadow will diffuse and disappear as the light is scattered. Accordingly, typical techniques now consist of illuminating the breast and mechanically manipulating the skin to try to bring every region of interest within 1 cm. of the skin. This is not easy to do, however, and large fractions of breast tissue which are actually at risk are inaccessible to detection of cancer or lesions by this technique. For these reasons, diaphanography has had limited application heretofore for diagnostic purposes, and has not supplanted other techniques employing X-rays or the like which have the potential of harming a patient that is being examined.

SUMMARY OF THE INVENTION

The present invention is based upon the recognition that transillumination of the breast with optical or near optical wavelength radiation provides information at the exit or light-emergence side of the breast that can be used to generate a perfectly good optical shadowgram, except that the information is heavily obscured by scatter. By rejecting such scatter, therefore, an optical equivalent of an X-ray mammogram can be produced without the use of any ionizing radiation.

In accordance with the present invention, the breast to be examined is compressed to a uniform thickness between two optically transparent planes of material, thereby to minimize light scatter in the thicker parts of the breast. An optical arrangement is employed which, in essence, collects all primary radiation, i.e., radiation which passes directly through the breast, and rejects all scattered radiation. The collected primary radiation is directed onto a light sensitive detector to produce electrical signals that are representative of the useful information in the light which is emergent from the breast, and those signals are employed to produce a visual image that can be used for diagnostic purposes.

In short, although the human breast is very dense optically, and strongly scatters radiation in nonionizing wavelengths, the present invention provides methods and and apparatus for obtaining a good shadowgraph by transillumination of the breast with nonionizing radiation, and by applying a good scatter rejecting geometry to that fraction of the incident light which emerges from the breast.

BRIEF DESCRIPTION OF THE DRAWINGS

The foregoing objects, advantages, construction and operation of the present invention will become more readily apparent from the following description and accompanying drawings wherein.

DESCRIPTION OF THE PREFERRED EMBODIMENTS

Upon illumination of a human breast with optical or near optical wavelength radiation, about 0.05% of the incident light energy will be transmitted without scatter. This being the case, a flying spot scanner designed to have a very efficient scatter rejection can circumvent the problem of scatter discussed previously. The same applies to a line scan system, a resolution line detector, and one-dimensional scatter removal slit system. It is possible, moreover, to apply these same principles to a two-dimensional system with a two-dimensional collimator system, although such an approach is far more difficult.

In any event, although the human breast is very dense optically and strongly scatters radiation in nonionizing wavelengths, one can obtain a good shadowgraph by applying a good scatter rejecting geometry. Such geometry can be effected, for example, by use of a flying spot scanner having post collimation if required; or by use of a line scanner where a full line of the object is illuminated, a linear post collimator is employed, and a high resolution line detector is used for imaging; or by an area illuminator that is associated with an area detector having a good two-dimensional collimator.

Figure 1:
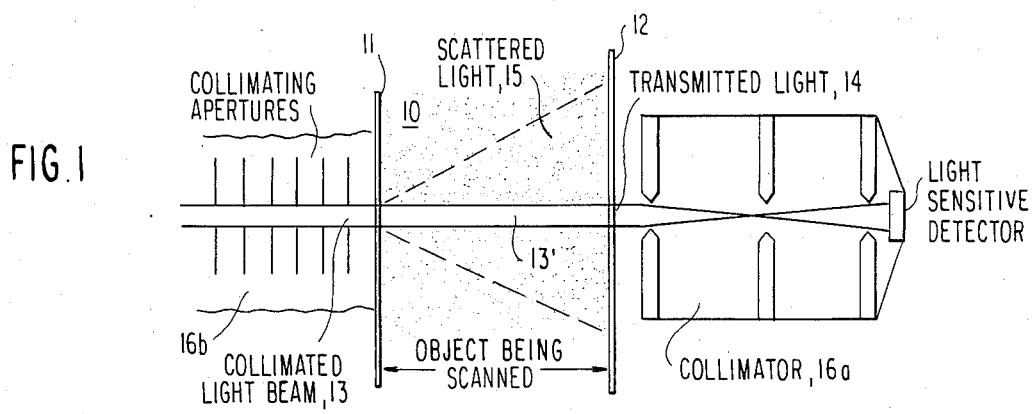
FIG. 1 diagrammatically depicts a method and apparatus in accordance with the present invention.

FIG. 1 depicts a method and apparatus of the type contemplated by the present invention using point scanning. A small fraction of the breast is illuminated with highly collimated light. The signature of the unscattered light that is to be collected is that it exits the breast directly opposite the entrance point and has an angular divergence no greater than the input light. The light so collected is directed onto a light sensitive detector which yields information about the optical transmission of a single spot. The entire breast can be imaged by raster scanning.

Referring more particularly to FIG. 1, the breast (or portion of the breast) 10 to be examined is compressed to a uniform thickness between two optically transparent planes of material 11 and 12, thereby to shape the breast or the breast portion being examined in a configuration having a pair of flat sides that are disposed adjacent planes 11, 12 respectively in spaced substantially parallel relation to one another.

Such compression of the breast is important to minimize light scatter in the thicker parts of the breast.

A collimated light beam 13 is provided by a source which may take any of many different forms, and is incident on one side of the compressed breast 10 as illustrated in FIG. 1. The collimated light beam can easily be effected by collimating apertures or slits as shown in FIG. 1, or with lenses and a point source, or with lasers with or without lenses and apertures. As light beam 13 traverses the object 10 being examined, photons are repeatedly scattered out of (and back into) the undeflected optical path 13'. At the other side of the object 10, therefore, i.e., adjacent plane 12, there will be a central region of transmitted light (designated 14 in FIG. 1) that is surrounded by a large halo of scattered light 15 whose radius is approximately equal to the thickness of object 10 between planes 11 and 12.

Figure 2:
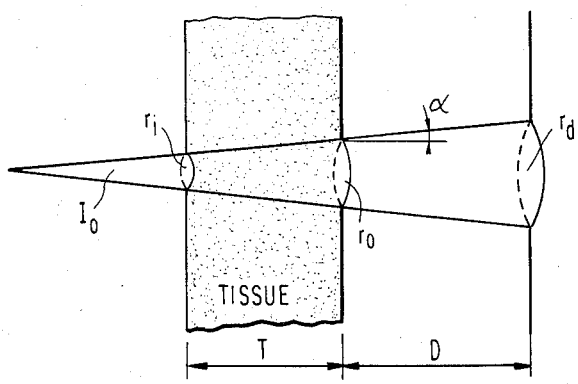
FIG. 2 illustrates the geometrical considerations utilized in the present invention.

If one places a light sensitive detector and a post-collimator 16a directly opposite the pre-collimator 16b, and in linear alignment therewith, then by careful design of the post-collimator all of the transmitted light 14 can be collected and only a small fraction of the scattered light will be seen by the detector. As an estimate of the scatter rejection requirement, the following calculation can be made:

Referring to FIG. 2, assume that a beam of light having a flux of $I_o$ photons/cm$^2$ and an angular spread $\alpha$ is incident on an aperture having a radius $r_i$ at the entrance plane of a body of tissue being examined, that said body of tissue has a thickness $T$, that the light emerges from the exit plane of said body of tissue at an exit aperture having a radius $r_o$, and that the light emerging from said exit aperture $r_o$ is directed onto a detector diaphragm having a radius $r_d$, the detector diaphragm aperture $r_d$ being spaced from the exit plane of said body of tissue by the distance $D$. If we designate $\epsilon$ as the fraction of the beam passing through the tissue which is unscattered, the flux of the unscattered photons is $$\frac{I_o \epsilon \pi r_i^2}{\pi r_o^2}$$

where $r_o = r_i + T \tan \alpha$. The flux of the scattered photons is approximately $$\frac{I_o(1 - \epsilon)\pi r_i^2}{\pi(r_i + T^2)}$$

If all photons passing through the detector aperture $r_d$ are detected, then the number of detected unscattered photons is $$N_u = I_o \epsilon \pi r_i^2$$

and the number of scattered photons is $$N_s = \frac{I_o(1 - \epsilon)\pi r_i^2 \pi (r_i + T \tan \alpha)^2 [r_i + (T + D) \tan \alpha]^2 \pi}{\pi(r_i^2 + T^2)(4\pi D^2)}$$

The ratio of the unscattered to scattered photons is $$\frac{N_u}{N_s} = \frac{\epsilon 4}{(1 - \epsilon)} \frac{D^2(r_i^2 + T^2)}{(r_i + T \tan \alpha)^2 [r_i + (T + D) \tan \alpha]^2}$$

A parametric study of the above equation indicates the ratio of unscattered to scattered photons increases rapidly as the angle $\alpha$ is made smaller (i.e. by improving the beam collimation or by use of a laser), and/or as $r_i$ is made smaller (the use of a small spot is highly desirable in any event for good resolution), and/or by increasing the distance $D$ (i.e. by providing better scatter rejection).

Referring again to FIG. 1, there are many forms of collimators, both mechanical and optical, which are already known to those skilled in the art, that can be used to effect the principles discussed above. The light which is incident, via collimator 16a, on the light sensitive detector will yield information about the optical transmission of a single spot, and the entire breast can be imaged by raster scanning, e.g., the incident collimated light beam 13 can be produced by a flying spot scanner to provide information about successive points along a given line, and the light source and collimator 16a, 16b can be moved relative to the compressed breast in a direction that is at right angles to the scan direction of the flying spot beam thereby to generate plural such lines of information. The electrical signals which are produced by the output detector can be processed to generate an image by any of many known techniques, one of which will be discussed hereinafter in reference to FIG. 5.

Line scanning, instead of point scanning, can be employed if desired. The arrangement utilized is identical to that described by reference to FIG. 1, except that a line of radiation is used instead of a point, the pre-collimator and post-collimator provide one-dimensional collimation instead of two, and the detector has spatial resolution in one dimension.

Figure 3:
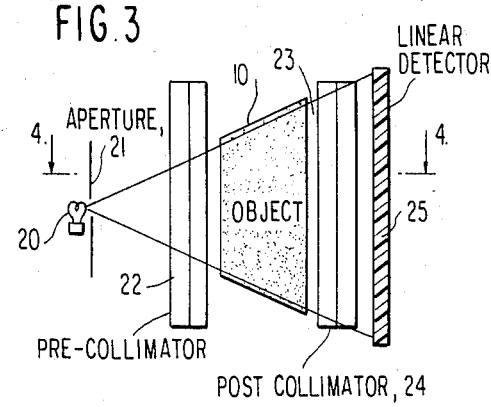
FIG. 3 depicts a method and apparatus in accordance with the present invention wherein a linear detector is employed for purposes of effecting line scanning.
Figure 4:
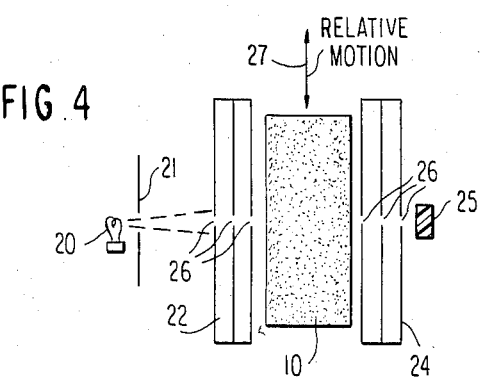
FIG. 4 is a view taken on line 4—4 of FIG. 3.

FIGS. 3 and 4 depict the present invention as practiced in a line scanning embodiment. A light source 20 cooperates with an aperture 21 and a pre-collimator 22 to produce a fan beam of light 23 that passes through the object 10 being examined and a post-collimator 24 onto a linear detector 25. The pre- and post-collimators assure that the only light rays that reach linear detector 25 are those which are not scattered out of the plane of the collimator slits 26 by more than an angle which is a design parameter of the slit. The linear detector 25 can be a high resolution linear array of photodiodes which yield a one-dimensional electronic image of the area of the breast being scanned. The second dimension is achieved by scanning the source, aperture, pre- and post-collimators, and the linear detector with respect to the breast as generally designated at 27.

Linear detector 25 could, if desired, be a two-dimensional piece of film. The image would then be recorded in a manner similar to that described above, except that the film would remain stationary.

Figure 5:
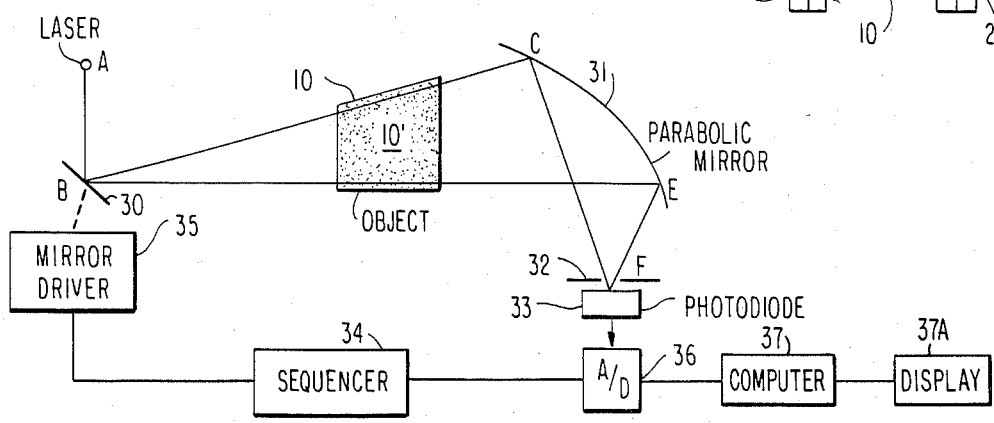
FIG. 5 diagrammatically illustrates another embodiment of the invention.

FIG. 5 depicts another embodiment of the invention. Instead of using a noncoherent light source as in FIGS. 3 and 4, the light source in FIG. 5 takes the form of a laser at point A. Light emitted from the laser reflects from a mirror 30 at point B, penetrates the compressed breast 10 in the region designated 10', reflects off of a parabolic mirror 31, and passes through an aperture 32 onto a photodiode 33. Two alternate light paths are depicted in FIG. 4, i.e., ABCF and ABEF. The light will take these various paths depending upon the angle of rotation of mirror 30. If light is scattered in the breast 10, the angle at which light emergent from the breast strikes parabolic mirror 31 will be changed, and the light reflected from mirror 31 will not enter aperture 32 at point F. The overall arrangement is made in such fashion that undeviated light rays pass through aperture 32, but scattered rays cannot.

In practice, the overall system includes a sequencer 34 which cooperates with a mirror driver 35 to drive mirror 30 about an axis that is perpendicular to the plane of the drawing. This causes the light to scan a long narrow region of the compressed breast 10. The light seen by photodiode 33 is read using standard electronics, e.g., an analog to digital converter 36 which supplies signals to a computer 37, and simultaneously recorded with the angle of mirror 30, i.e., the light beam direction. The information is sampled many thousands of times during each sweep across the region of interest, whereafter the apparatus is translated with respect to the breast 10 to create the second dimension of the scan. A visual image can then be generated from the digitally recorded transmission data in known fashion, e.g., by electronic reconstruction of the digital data to drive display 37a.

By way of summary, the present invention relies on the recognition that, in breast transillumination, the scattered radiation greatly exceeds the transmitted radiation. The invention provides a solution to this problem by creating an illuminating beam that is well characterized in its spatial and angular extent; and, upon exiting the breast, the unscattered radiation is separated from the scattered radiation by accepting only radiation within a given spatial and angular region. The implementation of the invention can take numerous forms, some of which have been discussed, e.g., point scanning using the focusing properties of a parabola, line scanning utilizing one-dimensional collimators and a high resolution one-dimensional detector, image display by electronic reconstruction of digital data, hard copy of those data, or analog storage on film, the use of both coherent and noncoherent light sources, etc. Many variations will be apparent to those skilled in the art, however, and it must therefore be understood that the foregoing description is intended to be illustrative only and not limitive of the present invention.

Having thus described my invention I claim:

1. Diaphanography apparatus for examining a human breast comprising:
  (a) first means for compressing the breast to be examined into a configuration having a pair of flat sides that are disposed in spaced substantially parallel relation to one another,
  (b) a light source operative to direct a beam of collimated light along a linear input path into incidence with one of said flat sides,
  (c) light collecting means comprising a light sensitive detector operative to generate electrical output signals in response to light that is incident on said detector,
  (d) said light sensitive detector being positioned to detect light which emerges from the other of said flat sides along an output path which is colinear with said input path,
  (e) said light collecting means including light scatter-rejection means for preventing light that emerges from the other of said flat sides along paths other than said output path or with angular deviation greater than an angular deviation of the beam of collimated light from impinging on said light sensitive detector,
  (f) means for effecting relative movement between said first means and said beam of light, and
  (g) means responsive to the signals that are generated by said light sensitive detector for producing a visible image.

2. The apparatus of claim 1 wherein said light scatter rejection means comprises a light collimator.

3. The apparatus of claim 1 wherein:
said light sensitive detector is of elongated configuration,
said relative motion being effected in a direction transverse to the direction of elongation of said detector.

4. The apparatus of claim 1 wherein:
the light scatter rejection means includes mirror means disposed between said other of said flat sides and said light collecting means for reflecting said emerging light toward said light sensitive detector, and
light blocking means including an aperture through which said emerging light passes, said aperture being located between said mirror means and said light sensitive detector.

5. The apparatus of claim 4 wherein said light source comprises a laser.

6. The apparatus of claim 4 wherein said mirror means comprises a parabolic mirror.

7. The apparatus of claim 1 wherein said light source comprises a laser.

8. Diaphanography apparatus for examining a human breast comprising first means for compressing the breast to be examined into a configuration having a pair of flat sides that are disposed in spaced substantially parallel relation to one another, a light source operative to direct a beam of collimated light along a linear input path into incidence with one of said flat sides, light collecting means comprising a light sensitive detector operative to generate electrical output signals in response to light that is incident on said detector, said light sensitive detector being positioned to detect light which emerges from the other of said flat sides along an output path which is colinear with said input path, said light collecting means including light scatter-rejection means for preventing about 99.5% of said beam of collimated light which emerges from the other of said flat sides along paths other than said colinear path or with angular divergence greater than angular divergence of said beam of collimated light from impinging on said light sensitive detector, means for effecting relative movement between said first means and said beam of light, and means responsive to the signals that are generated by said light sensitive detector for producing a visible image.

9. The apparatus of claim 8 wherein said light scatter rejection means comprises a light collimator.

10. The apparatus of claim 8 wherein said light sensitive detector is of elongated configuration, said relative motion being effected in a direction transverse to the direction of elongation of said detector.

11. The apparatus of claim 8 wherein the light scatter rejection means includes mirror means disposed between said other of said flat sides and said light collecting means for reflecting said emerging light toward said light sensitive detector and light blocking means including an aperture through which said emerging light passes, said aperture being located between said mirror means and said light sensitive detector.

12. The apparatus of claim 11 wherein said mirror means comprises a parabolic mirror.

13. The apparatus of claim 11 wherein said light source comprises a laser.

14. The apparatus of claim 8 wherein said light source comprises a laser.

15. The method of generating an image of the human breast by transillumination, comprising the steps of:
compressing a human breast to a uniform thickness,
directing a collimated beam of light with a given angular spread toward one side of said compressed breast along a path,
effecting relative motion between said light beam and said compressed human breast by scanning said collimated beam of light along a predetermined direction at said one side of said compressed breast,
collecting light which emerges from the other side of said compressed breast without scatter while rejecting the emergent light which has passed through the compressed breast with scatter by collecting only that light which emerges from the other side of said compressed breast along a theoretical extension of said path and with an angular spread no greater than an angular spread of said collimated beam of light, and
directing said collected light onto a radiation detector.

16. The method of claim 15 wherein said radiation detector is a sheet of film.

17. The method of claim 15 wherein said radiation detector is operative to generate electrical signals, and where said method further includes utilizing said electrical signals to produce a visual image.

18. The method of claim 17 wherein said step of producing a visual image comprises storing digital data representative of predetermined parameter values of said electrical signals, and effecting electronic reconstruction of said stored digital data to generate a visual image.

19. The method of claim 15 wherein said collecting step comprises placing a post-collimator adjacent the other side of said compressed breast, the post-collimator being operative to permit the passage therethrough of only that light which emerges from a predetermined restricted area of the other side of said compressed breast with an angular spread which is no greater than the angular spread of the collimated beam of light.

20. The method of claim 19 wherein said predetermined restricted area is substantially a point.

21. The method of claim 19 wherein said predetermined restricted area is a line.

22. The method of claim 15 wherein said step of directing a collimated beam of light includes providing a laser light source.

23. The method of generating an image of the human breast by transillumination, comprising the steps of compressing a human breast to a uniform thickness, with a given angular spread toward one side of said compressed breast, effecting relative motion between said light beam and said compressed human breast by scanning said collimated beam of light along a predetermined path at said one side of said compressed breast, collecting about 0.05% of said collimated beam of light which emerges from the other side of said compressed breast without scatter while rejecting about 99.5% of said collimated beam of light emergent from the compressed breast with scatter by collecting only that light which emerges from the other side of said compressed breast with an angular spread no greater than the angular spread of said collimated beam of light, and directing said collected light onto a radiation detector.

24. The method of claim 23 wherein said radiation detector is a sheet of film.

25. The method of claim 23 wherein said radiation detector is operative to generate electrical signals, and the method further includes using said electrical signals to produce a visual image.

26. The method of claim 25 wherein said step of producing a visual image comprises storing digital data representative of predetermined parameter values of said electrical signals, and effecting electronic reconstruction of said stored digital data to generate a visual image.

27. The method of claim 23 wherein said collecting step is operative to collect only that light which emerges from the other side of said compressed breast at a point that is directly opposite the point on which said input beam is incident.

28. The method of claim 23 wherein said collecting step comprises placing a post-collimator adjacent the other side of said compressed breast, the post-collimator being operative to permit the passage therethrough of only that light which emerges from a predetermined restricted area of the other side of said compressed breast with an angular spread which is no greater than the angular spread of the collimated beam of light.

29. The method of claim 28 wherein said predetermined restricted area is substantially a point.

30. The method of claim 28 wherein said predetermined restricted area is a line.

31. The method of claim 23 wherein said step of directing a collimated beam of light includes providing a laser light source.

* * * * *